(12) United States Patent
Termanini et al.

(10) Patent No.: US 10,441,436 B2
(45) Date of Patent: Oct. 15, 2019

(54) ACETABULAR CUP EXTRACTOR

(71) Applicant: HIP INNOVATION TECHNOLOGY, LLC., Boca Raton, FL (US)

(72) Inventors: Zafer Termanini, Port Saint Lucie, FL (US); Brian Vanhiel, Smyrna, GA (US); Adam Ambrecht, Kennesaw, GA (US)

(73) Assignee: HIP INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 15/742,292

(22) PCT Filed: Jul. 15, 2016

(86) PCT No.: PCT/US2016/042445
§ 371 (c)(1),
(2) Date: Jan. 5, 2018

(87) PCT Pub. No.: WO2017/019332
PCT Pub. Date: Feb. 2, 2017

(65) Prior Publication Data
US 2018/0193166 A1   Jul. 12, 2018

Related U.S. Application Data

(60) Provisional application No. 62/197,224, filed on Jul. 27, 2015.

(51) Int. Cl.
*A61F 2/46* (2006.01)
*A61B 17/16* (2006.01)
*A61F 2/34* (2006.01)

(52) U.S. Cl.
CPC ........ *A61F 2/4609* (2013.01); *A61B 17/1666* (2013.01); *A61F 2002/3483* (2013.01); *A61F 2002/4619* (2013.01)

(58) Field of Classification Search
CPC ................................ A61F 2/4609; A61F 2/605
See application file for complete search history.

(56) References Cited

U.S. PATENT DOCUMENTS

| 4,729,270 A * | 3/1988 | Pritchard | ................ B25B 13/00 |
| | | | 81/177.5 |
| 6,565,575 B2 * | 5/2003 | Lewis | ................ A61B 17/1666 |
| | | | 606/99 |

(Continued)

FOREIGN PATENT DOCUMENTS

WO       2015155657 A1    10/2015

OTHER PUBLICATIONS

International Search Report for corresponding application PCT/US2016/042445 dated Oct. 7, 2016.

(Continued)

*Primary Examiner* — Andrew Yang
(74) *Attorney, Agent, or Firm* — Norris McLaughlin PA

(57) ABSTRACT

A surgical tool and method used to extract an acetabular cup from an acetabulum with minimal or no bone damage even if there has been significant bone ingrowth prior to the extraction process. The tool is designed for use with a reverse hip prosthesis wherein the acetabular cup comprises a stem extending from its concave surface and an acetabular ball is affixed to the stem. The tool is rotated on the ball and a blade is thereby caused to rotate adjacent or in close proximity to a convex surface of the cup in a position between the acetabular bone and the cup, thereby separating the cup from the bone.

11 Claims, 3 Drawing Sheets

(56) References Cited

U.S. PATENT DOCUMENTS

| | | | |
|---|---|---|---|
| 8,313,531 B2 * | 11/2012 | Termanini | A61F 2/34 623/22.15 |
| 2005/0131414 A1 | 6/2005 | Chana | |
| 2008/0195111 A1 | 8/2008 | Anderson | |
| 2011/0054628 A1 | 3/2011 | Banks et al. | |
| 2012/0184964 A1 | 7/2012 | Hudak, Jr. et al. | |
| 2015/0313722 A1 | 11/2015 | Hudak, Jr. | |

OTHER PUBLICATIONS

Written Opinion of the International Searching Authority for corresponding application PCT/US2016/042445 dated Oct. 7, 2016.

\* cited by examiner

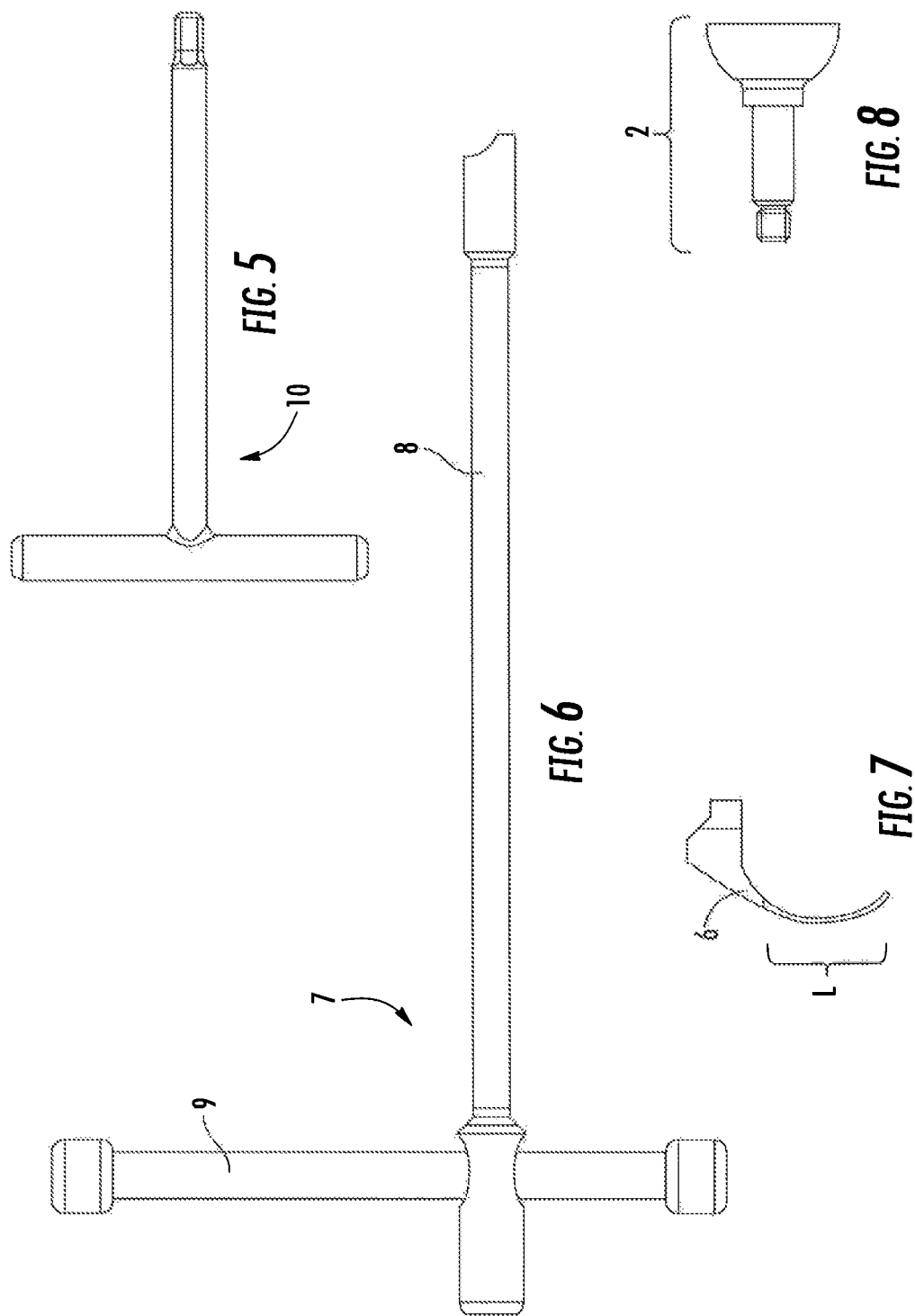

ACETABULAR CUP EXTRACTOR

This is an application filed under 35 USC 371 based on PCT/US2016/042445 filed 15 Jul. 2016, which in turn claims priority to U.S. Ser. No. 62/197,224 filed 27 Jul. 2015. The present application claims the full priority benefit of these prior applications and herein incorporates by reference the full disclosures of these prior applications as if set forth herein.

BACKGROUND OF THE INVENTION

Field of the Invention

The present invention relates to surgical instruments used in connection with a reverse hip prosthesis. More particularly, the invention has to do with a surgical tool for extracting an acetabular cup from an acetabulum.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, an acetabular ball is affixed on a stem extending from the bottom of the concave surface of the acetabular cup. The surgical tool of the invention enables a surgeon to remove the acetabular cup by pressing the distal end of the tool against the acetabular ball while carefully rotating the tool on the ball to cause a blade to separate the cup from the acetabulum. In the present disclosure, we use the term "acetabular cup extractor" from time to time to describe the surgical tool of the invention.

BRIEF DESCRIPTION OF THE DRAWINGS

FIG. 5 is an elevation view of a driver used with the surgical tool of the invention.

FIG. 6. Is an elevation view of a handle used with the surgical tool of the invention.

FIG. 7 is an elevation view of a blade used with the surgical tool of the invention.

FIG. 8 is an elevation view of an extractor cup used with the surgical tool of the invention.

DESCRIPTION OF THE PREFERRED EMBODIMENT

Figure 1:
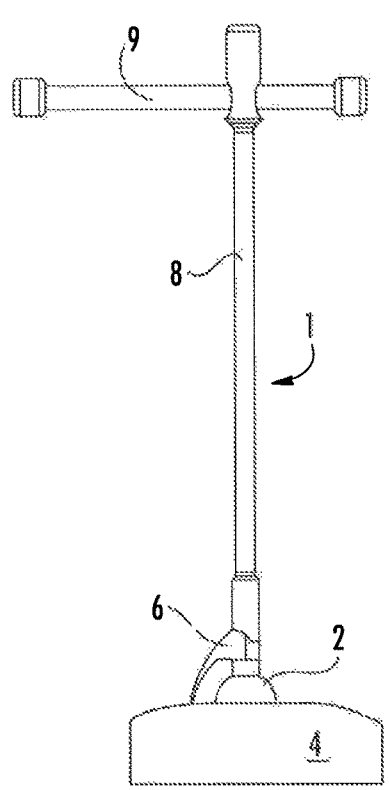
FIG. 1 is an elevation view of the surgical tool of the invention positioned on an implanted acetabular cup.
Figure 2:
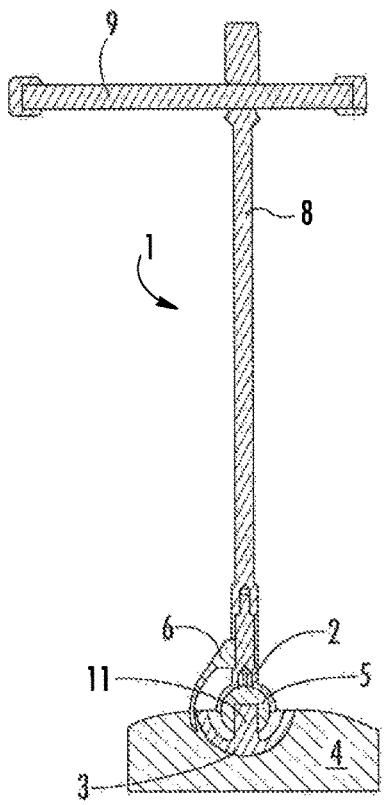
FIG. 2 is a section view of FIG. 1.
Figure 3:
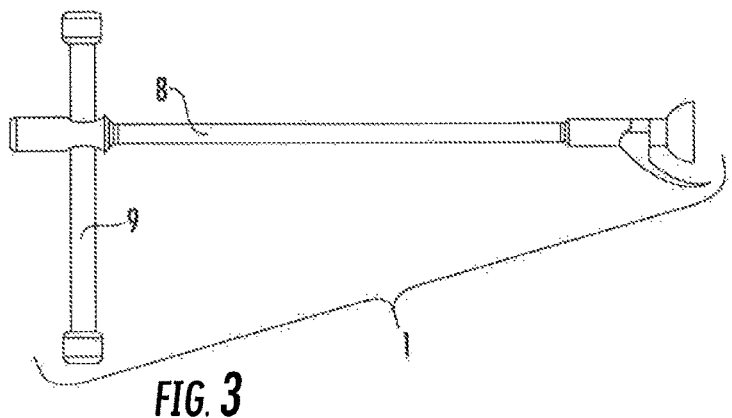
FIG. 3 is an elevation view of the surgical tool of the invention.
Figure 4:
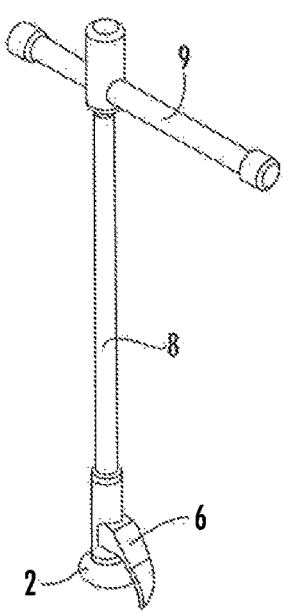
FIG. 4 is a perspective view of the surgical tool of the invention.

The acetabular cup extractor 1 is illustrated in elevation in FIG. 3 and in perspective in FIG. 4. In FIGS. 1 and 2, elevation and section views, respectively, the extractor 1 is positioned on an acetabular ball 5 which is affixed to the stem 11 of acetabular cup 3. The acetabular cup 3 is implanted in acetabular bone 4. The extractor cup 2 is in articulating contact with acetabular ball 5 and the distal end of blade 6 is positioned between the convex outer surface of cup 3 and bone 4. In the surgical method of the invention, the extractor cup 2 is carefully rotated on acetabular ball 5 to cause blade 6 to move along or in close proximity to the convex surface of acetabular cup 3, thereby rotating the blade 6 around the convex surface and adjacent or in close proximately to said surface so that the blade is between the acetabular cup 3 and the acetabulum. This movement causes the bone 4 of the acetabulum to be separated from the cup 3. Thus, the surgeon pushes the acetabular cup extractor 1 downwardly so that the extractor cup 2 contacts the acetabular ball 5 and a distal portion of blade 6 is caused to move into acetabular bone 4 in a position adjacent or in close proximity to the convex surface of acetabular cup 3. The depth of the distal portion of blade 6 in bone 4 is maintained as the acetabular cup extractor 1 is rotated. Blade 6 comes in various sizes such that the portion of the blade designated as "L" in FIG. 7 varies in length. Multiple blades of different lengths can be used, always starting with the shortest blade length, then using the next longest length, etc. For example, if three blades are used, the shortest length blade is used first and at least one complete rotation of the blade between the acetabular cup 3 and the bone 4 is completed. In other words, the blade 6 is rotated at least 360 degrees around the cup. Then the next longest blade length is used and at least one complete rotation of the blade between the acetabular cup 3 and bone 4 is completed. This process is repeated with the next longest blade, i.e. the longest of the three blades, thereby loosening the connection between the acetabular cup 3 and bone 4 so that the acetabular cup 3 is sufficiently loosened that it can be lifted out of bone 4. Since blade 6 moves adjacent or in close proximity to the convex surface of acetabular cup 3, bone damage is minimized even if there has been significant bone ingrowth prior to the removal process. The process is conducted carefully in order to minimize the risk of damage to the bone.

In addition to the extractor cup 2 and blade 6, the acetabular cup extractor 1 is comprised of a handle 7 made of a shaft 8 and a movable lever arm 9 as shown in FIG. 6. The lever arm facilitates rotation of extractor 1 while maintaining downward pressure on extractor 1.

Figure 9:
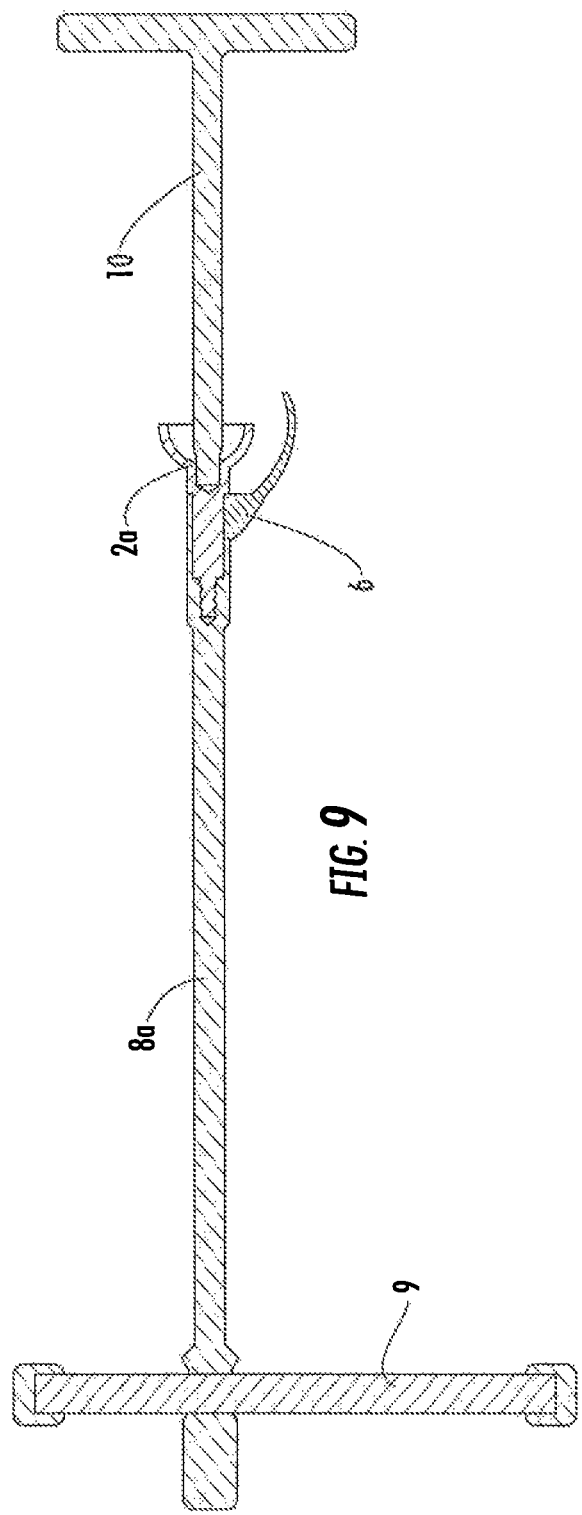
FIG. 9 is a section view of the acetabular cup extractor of FIG. 3 and the driver of FIG. 5.

Driver wrench 10, illustrated in elevation in FIG. 5, is used to fasten and unfasten the extractor cup 2a to and from shaft 8 of handle 7. Extractor cup 2a is an optional embodiment which is threaded into shaft 8a as illustrated in section in FIG. 9 (The extractor cup 2 of FIG. 8 is snap fit into shaft 8.) A section view illustrating the position of these elements in the fastening and unfastening operations is provided in FIG. 9.

In the surgical method of the invention, any screws or other connectors extending from acetabular cup 3 into bone 4 are removed. If necessary, acetabular ball 5 is removed in order to gain access to the screws. Then acetabular ball 5 is placed back on the stem of the acetabular cup and the cup removal process is continued. Blade 6 is then pushed into the bone adjacent the convex surface of the acetabular cup until the extractor cup 2 is in contact with acetabular ball 5. While pressing the extractor cup 2 against the acetabular ball 5, the acetabular cup extractor 1 is rotated on acetabular ball 5, thereby causing blade 6 to loosen the connection between acetabular cup 3 and the bone 4. When the acetabular cup 3 is sufficiently loosened from bone 4 after using blades 6 of increasing length as explained above, the acetabular cup is lifted out of the bone.

The acetabular cup removal tool of the invention may be included in a kit comprising other surgical tools and/or implants.

The invention claimed is:

1. A surgical tool adapted for removing an acetabular cup from an acetabulum wherein the acetabular cup is a component of a reverse hip prosthesis and comprises an acetabular ball affixed to a stem which extends from a concave surface of the acetabular cup, the surgical tool comprising:
   a shaft;
   an extractor cup affixed at its proximal end to a distal end of the shaft, the extractor cup having at its distal end a concave surface sized to articulate on the acetabular ball; and
   a blade having a proximal end affixed to the shaft and a distal portion sized to move adjacent or in close proximity to a convex surface of the acetabular cup, the convex surface of the acetabular cup being in contact with the acetabulum; and,
   a detachable driver wrench adapted to affix the extractor cup to the shaft.

2. The surgical tool of claim 1 further comprising a lever arm movably positioned in the shaft and adapted to facilitate rotation of the tool while maintaining downward pressure on the tool.

3. A kit containing the surgical tool of claim 1.

4. A method of using the surgical tool of claim 1 comprising placing the concave surface of the extractor cup into articulating contact with the acetabular ball and causing the distal portion of the blade to move into the acetabulum in a position adjacent or in close proximity to a convex surface of the acetabular cup and then rotating the extractor cup on the acetabular ball, thereby rotating the blade around the convex surface of the acetabular cup and between the cup and the acetabulum until the acetabular cup is separated from the acetabulum.

5. The method of claim 4 whereby blades of increasing length are used sequentially until the acetabular cup is separated from the acetabulum.

6. A surgical tool adapted for removing an acetabular cup from an acetabulum wherein the acetabular cup is a component of a reverse hip prosthesis and comprises an acetabular ball affixed to a stem which extends from a concave surface of the acetabular cup, the surgical tool comprising:
   a shaft;
   an extractor cup concentrically affixed at its proximal end to a distal end of the shaft, with the extractor cup having at its distal end a concave surface sized to articulate on the acetabular ball;
   a blade having a proximal end affixed to the shaft and a distal portion sized to move adjacent or in close proximity to a convex surface of the acetabular cup, the convex surface of the acetabular cup being in contact with the acetabulum; and,
   a detachable driver wrench adapted to affix the extractor cup to the shaft.

7. The surgical tool of claim 6, wherein the extractor cup is mounted onto distal end of the shaft with a snap fit fitting.

8. The surgical tool of claim 6, wherein the extractor cup is mounted onto the distal end of the shaft with a threaded fitting.

9. A surgical tool adapted for removing an acetabular cup from an acetabulum wherein the acetabular cup is a component of a reverse hip prosthesis and comprises an acetabular ball affixed to a stem which extends from a concave surface of the acetabular cup, the surgical tool comprising:
   a handle having a shaft and a moveable lever arm which facilitates rotation of the shaft while maintaining downward pressure on an extractor cup which is affixed at its proximal end to a distal end of the shaft, with the extractor cup having at its distal end a concave surface sized to articulate on the acetabular ball; and
   a blade having a proximal end affixed to the shaft and a distal portion sized to move adjacent or in close proximity to a convex surface of the acetabular cup, the convex surface of the acetabular cup being in contact with the acetabulum; and
   detachable driver wrench adapted to affix the extractor cup to the shaft.

10. The surgical tool of claim 9, wherein the extractor cup is mounted onto distal end of the shaft with a snap fit fitting.

11. The surgical tool of claim 9, wherein the extractor cup is mounted onto the distal end of the shaft with a threaded fitting.

* * * * *